United States Patent [19]

Gentile

[11] 4,258,708
[45] Mar. 31, 1981

[54] ARTICULATED POSITIONING SYSTEM FOR DEVICES ADAPTED TO EXTERNALLY EXERT A HOLDING ACTION ON BONE TISSUES

[76] Inventor: Giulio Gentile, Via San Martino ai Monti, N.8, 00184 Rome, Italy

[21] Appl. No.: 925,159

[22] Filed: Jul. 17, 1978

Related U.S. Application Data

[63] Continuation-in-part of Ser. No. 801,305, May 27, 1977, Pat. No. 4,185,624.

[30] Foreign Application Priority Data

Jul. 22, 1977 [IT] Italy .............................. 50399 A/77

[51] Int. Cl.$^3$ .......................... A61F 5/04; A61B 17/18
[52] U.S. Cl. .................................................. 128/92 A
[58] Field of Search ................. 128/92 A, 92 R, 92 D, 128/92 B

[56] References Cited

U.S. PATENT DOCUMENTS

| | | | |
|---|---|---|---|
| 2,238,870 | 4/1941 | Haynes | 128/92 A |
| 2,346,346 | 4/1944 | Anderson | 128/92 A |
| 2,406,987 | 9/1946 | Anderson | 128/92 A |
| 3,961,854 | 6/1976 | Jaquet | 128/92 A |

FOREIGN PATENT DOCUMENTS 528089  9/1976  U.S.S.R. .............................. 128/92 A

Primary Examiner—Ronald L. Frinks
Attorney, Agent, or Firm—Schwartz, Jeffery, Schwaab, Mack, Blumenthal & Koch

[57] ABSTRACT

A device for externally exerting a holding action on bone tissues includes a plurality of means for engaging the bone and exerting a holding action thereon. The engaging and exerting means are connected by a central tubular body which is positioned with its axis perpendicular to the surface of the fracture. There are a plurality of clamping means interconnecting the two engaging and exerting means, the clamping means permitting rotational movement thereof and translation along shank portions of the clamping means. At least one of the clamping means can have an adjustable feature including an elongated cylindrical shank, the shank having a threaded axial hole therein and a longitudinal groove on the external surface thereof. The shank is slidably received within a hollow tubular body having a threaded end thereon. A cap is screwed on the threaded end. The body further has a substantially radial threaded hole therein with a first screw inserted in the radial hole and received in the groove. The shank also has an axial opening therein, and a second screw having a head positioned between the cap and the body extends into the axial opening of the shank.

5 Claims, 9 Drawing Figures

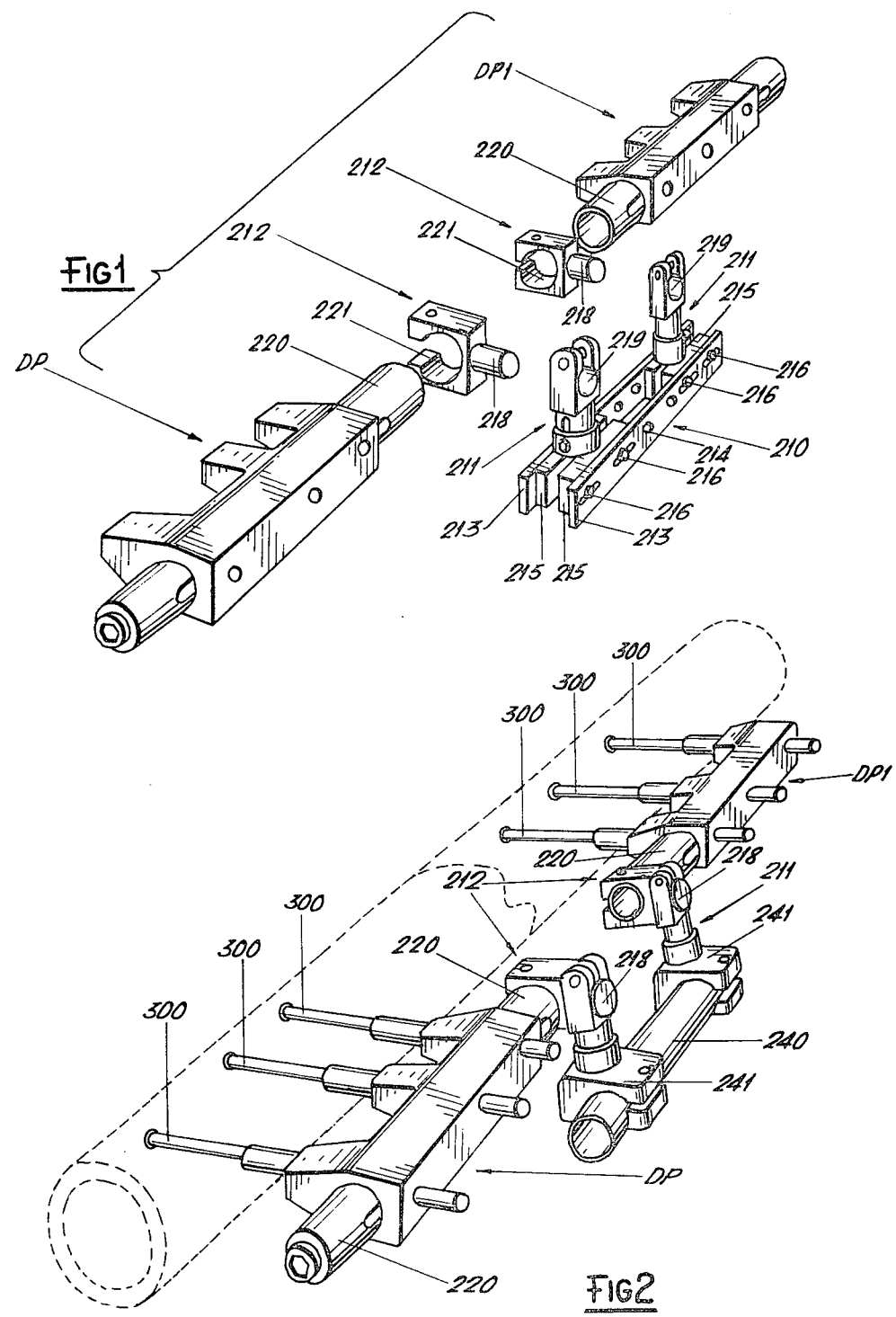

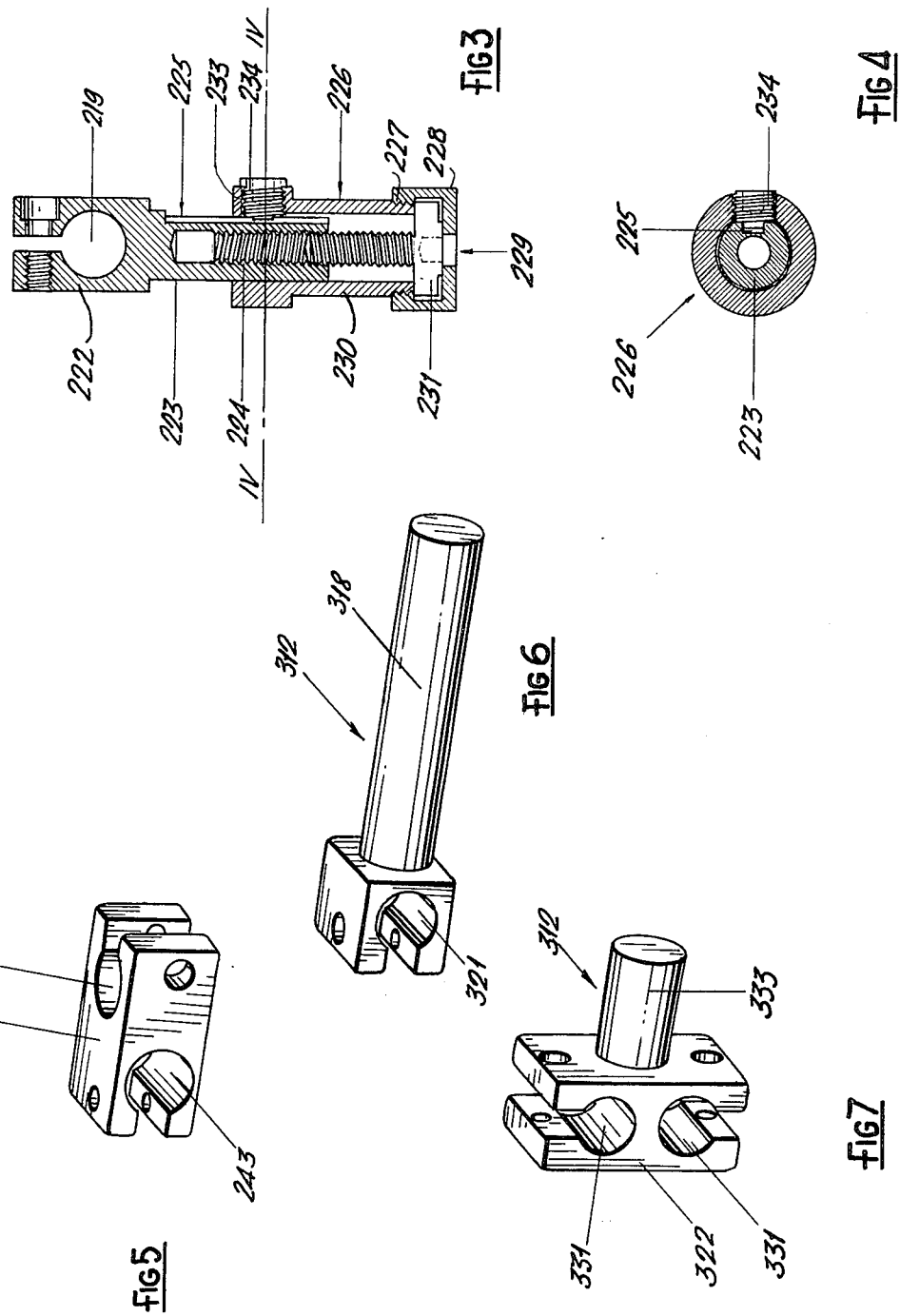

ARTICULATED POSITIONING SYSTEM FOR DEVICES ADAPTED TO EXTERNALLY EXERT A HOLDING ACTION ON BONE TISSUES

CROSS-REFERENCE

This is a continuation-in-part of Ser. No. 801,305, filed May 27, 1977, now U.S. Pat. No. 4,185,624.

This invention refers to a positioning system connecting devices to each which are adapted to externally exert a holding action on bone segments or fragments, particularly for connecting two or more holding devices as described in my patent application Ser. No. 801,305. More specifically, the invention refers to a plurality of joints which can be variously placed in order to allow the holding devices and thus the respective bone segments or fragments to be correctly positioned and forces in any direction to be applied thereto. The magnitude and direction of these forces can be varied also through separate unidirectional movements, and the assembly consisting of the holding devices and the joints can be kept substantially stationary during each movement.

The devices heretofore used, that is the external fixators, make it possible to connect to each other the holding devices applied to two or more fragments of a fracture, but they have the serious drawback that they allow the application of forces to the bone fragments only in obliged directions, which directions often do not correspond to the direction actually required, owing to the varying configuration and direction of the fracture surfaces. Furthermore, the relative position of the fragments in given directions can be varied only after the release of the connecting elements, thus annulling the previously applied force.

This drawback of said external fixators of the prior art is particularly serious in the treatment of oblique fractures and when, some time after the application thereof, biological conditions occur requiring the strength with which the bone fragments are gripped and held in mutual contact by the holding elements to be registered in order to maintain constantly the stability of the fixation.

The objects of the invention will be now described more specifically.

They are:

1. Providing a joint between the devices exerting a holding action on bone tissues which joint can generally position and fix these devices in any mutual relationship.

2. Firmly connecting to each other a plurality of holding devices for any position thereof, these devices being applied on the same bone segment or fragment, on the same side thereof or on two or more sides diametrically opposed with respect to the bone fragment on which the holding action is exerted.

3. Providing for the variation of the mutual position of the holding devices applied to two or more bone fragments so as to apply forces of any magnitude and direction to the respective fragments, in two different manners:

(a) as a consequence of a single movement obtained by positioning the joint or the assembly of joints so that one of the movements made possible thereby coincides with the direction of the forces to be applied thereto;

(b) as a resultant of two or more separate unidirectional movements in directions corresponding with or perpendicular to given reference planes.

4. Providing for the application of a force in a different direction, when the device is already under stress, while yet preventing the movements in any other direction.

5. Compensating the possible deviation of the applied force, caused by the flexibility of the holding devices, through movements tending to cause deviations in the opposite direction and using the inherent elasticity of the holding elements to improve the stability of the fixation and constantly maintain the applied force.

6. In order to achieve the above objects providing for the holding devices to be rotated about at least three axes perpendicular to each other and translated at least along the same axes, and obtaining these movements through a screw mechanism or levers provided with suitable handles.

7. Improving the stability of the fixation by applying correctly oriented forces which can be registered so as to prevent or eliminate any possible slack caused by variations of the elastic reaction of the bone and to avoid in all cases that the fixator becomes an inert article located in close proximity to a fracture.

How these and other objects are obtained by means of the system according to the invention will be disclosed in what follows referring to the annexed drawings wherein the joints of the invention and some possible uses thereof are shown as an absolutely nonlimitating example.

In the drawings:

FIG. 1 is a partially exploded perspective view of a positioning system connecting two holding devices as disclosed in my prior patent application;

FIG. 2 is a perspective view of the system of FIG. 1 making use of a modified element of connection;

FIG. 3 is a cross sectional view of one of the elements of the system adapted to perform a translatory movement along its own axis;

FIG. 4 is a sectional view along line IV—IV of FIG. 3;

FIG. 5 is a perspective view of a detail of one of the elements of the system;

FIG. 6 is a similar view of a second element of the system;

FIG. 7 is a similar view of a further element;

Figure 8:
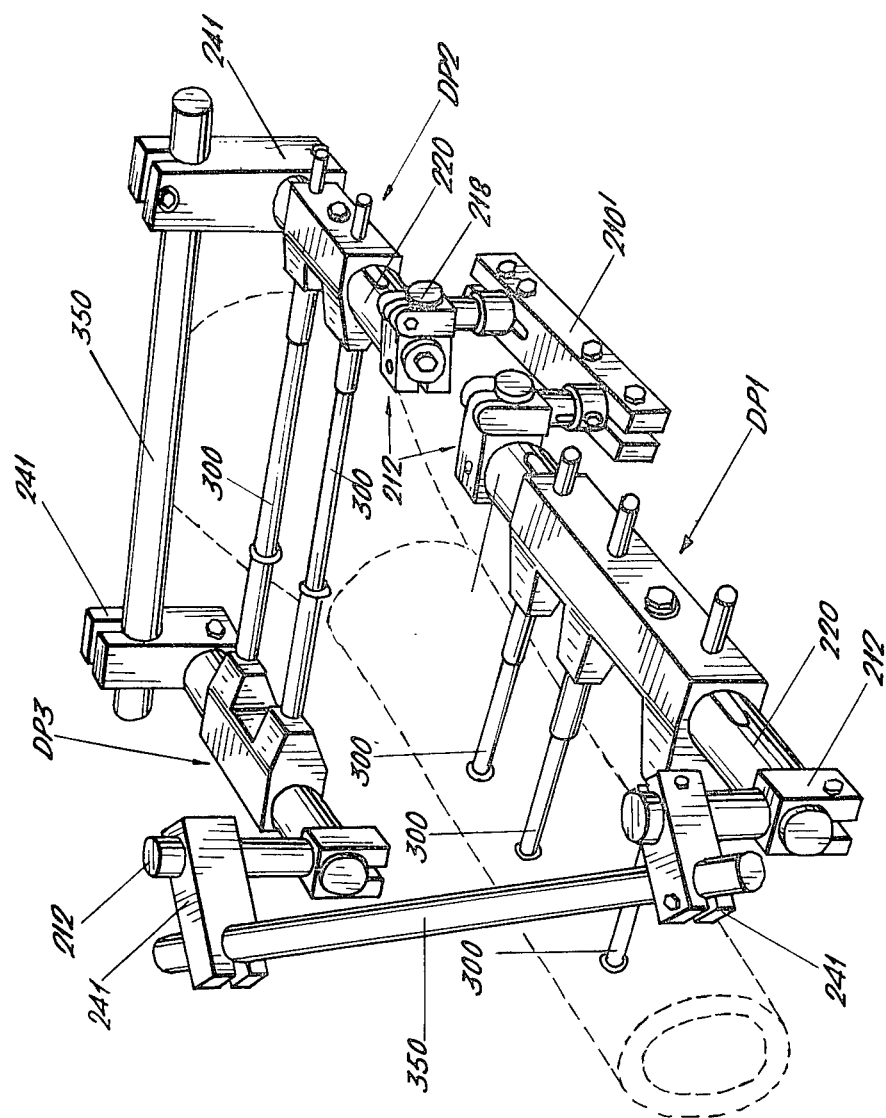
FIG. 8 is a perspective view showing one of the possible arrangements of the system.

As clearly seen in FIGS. 1, 2, 8 and 9, this improvement of my previous patent application Ser. No. 801,305 refers to an articulated system, for connecting to each other a plurality of holding devices, which system can be variously assembled according to the different biomechanical conditions which can occur in treating fractures, osteotomies, anthrodesis and to the above mentioned objects.

With reference to FIG. 1, two holding devices according to the main patent application, generally referred to with references DP and DP1, are connected to each other through a system comprising a connecting element 210, a pair of clamp members 211 having an adjustable shank, hereinafter called adjustable clamps, and a pair of clamp members 212 having a simple shank, hereinafter called simple clamps.

Connecting element 210 comprises a pair of elongated plates 213 provided with a plurality of aligned holes 214 and two locking blocks 215 each comprising two symmetrical halves forming a semicylindrical cavity. Blocks 215 are provided with pairs of transverse through holes receiving two nut and bolt units 216 received into holes 214 of plates 213. Preferably, the contact surfaces of blocks 215 or the blocks themselves can be of an insulating material having a certain elasticity for electrically insulating holding devices DP and DP1 from each other.

The jaws of the clamp members are provided with locking means adapted to lock the jaws themselves. In the arrangement shown in FIG. 1, shank 218 of each clamp 212 is received within jaw 219 of the corresponding clamp member 211. Cylindrical end 220 of each holding device DP and DP1 is similarly received within jaw 221 of the respective member 212.

The particular construction of member 211 is shown in FIG. 3. Member 211 comprises a clamp head 222 similar to the head of member 212 and a hollow cylindrical shank 223 internally threaded at 224 and provided with a longitudinal groove 225 on the outer face thereof. A hollow cylindrical element 226 is slidingly arranged externally of cylindrical shank 223, and it is concentric therewith, element 226 being provided with an externally threaded end 227 on which a cap element 228 is threaded which is provided with a hole 229 corresponding with the axis of shank 223. A socket screw 230 is threaded within threaded cavity 224. Head 231 of screw 230 abuts against the wall of cylindrical element 226 and cap element 228. Operation of screw 230 by means of an Allen wrench introduced into hole 229, will cause shank 223 to slide within cylindrical element 226, which is laterally provided with a radial threaded hole 233 into which a socket screw 234 is threaded, at the enlarged end thereof.

The mutual relationship of shank 223, cylindrical element 226 and screw 234 is more clearly seen in FIG. 4 which is a sectional view along line IV—IV of the device shown in FIG. 3. The end of screw 234 is received within groove 225 to avoid the relative rotation of elements 223 and 226. Moreover, abutting against the suitably flattened edges of groove 225, the head of screw 234 can fix the mutual position of elements 223 and 226, thus eliminating any slack therebetween.

FIG. 2 shows a modified system wherein connecting element 210 of FIG. 1 is replaced by a tubular element 240 which is connected to adjustable clamp members 211 through double clamp members 241.

A double clamp member, shown in FIG. 5, comprises a parallelepiped-shaped body provided with two jars 242 and 243, respectively, the axes thereof being perpendicular to each other.

FIG. 6 shows a detail of a single clamp member substantially identical with member 212 shown in FIG. 1. This member is referred to as 312 and comprises a jaw head 321 provided with a long shank 318.

FIG. 7 shows a type of double clamp 322 provided with a shank 333 wherein jaws 331 and 332 are located along parallel axes. Alternatively, shank 333 could also be eliminated. This clamp is particularly useful in an articulated system according to the invention for connecting two superposed holding devices which will be positioned according to the direction of jaws 331 and 332. These devices, however, can also be located at a variable angle to each other through a pivoting movement about the axes of the jaws. This clamp can be used as a part of a simplified joint for connecting two aligned holding devices DP and DP1.

FIG. 8 shows a second use of the elements of the system according to the invention. As already provided for in the main patent application, two holding devices can be applied on a bone segment or fragment, on two diametrically opposed sides thereof, for connecting the relative ends of pins 300. Pins 300 can also be different from the pins shown which pass through the bone side to side. As shown in FIG. 8, two holding devices DP2 and DP3 can be connected by a pair of clamps 241 and a bar 350.

A similar connection, obtained with different elements, is used for firmly connecting devices DP1 and DP3. In this case, a pair of clamp members 212, a pair of double clamps 241 and a bar 350 are used. It should also be noted that an element 210' slightly different from element 210 shown in FIG. 1 is shown in FIG. 8 as comprising an H-shaped single body, the ends of which are slotted and a jaw shaped to act as a clamp.

Figure 9:
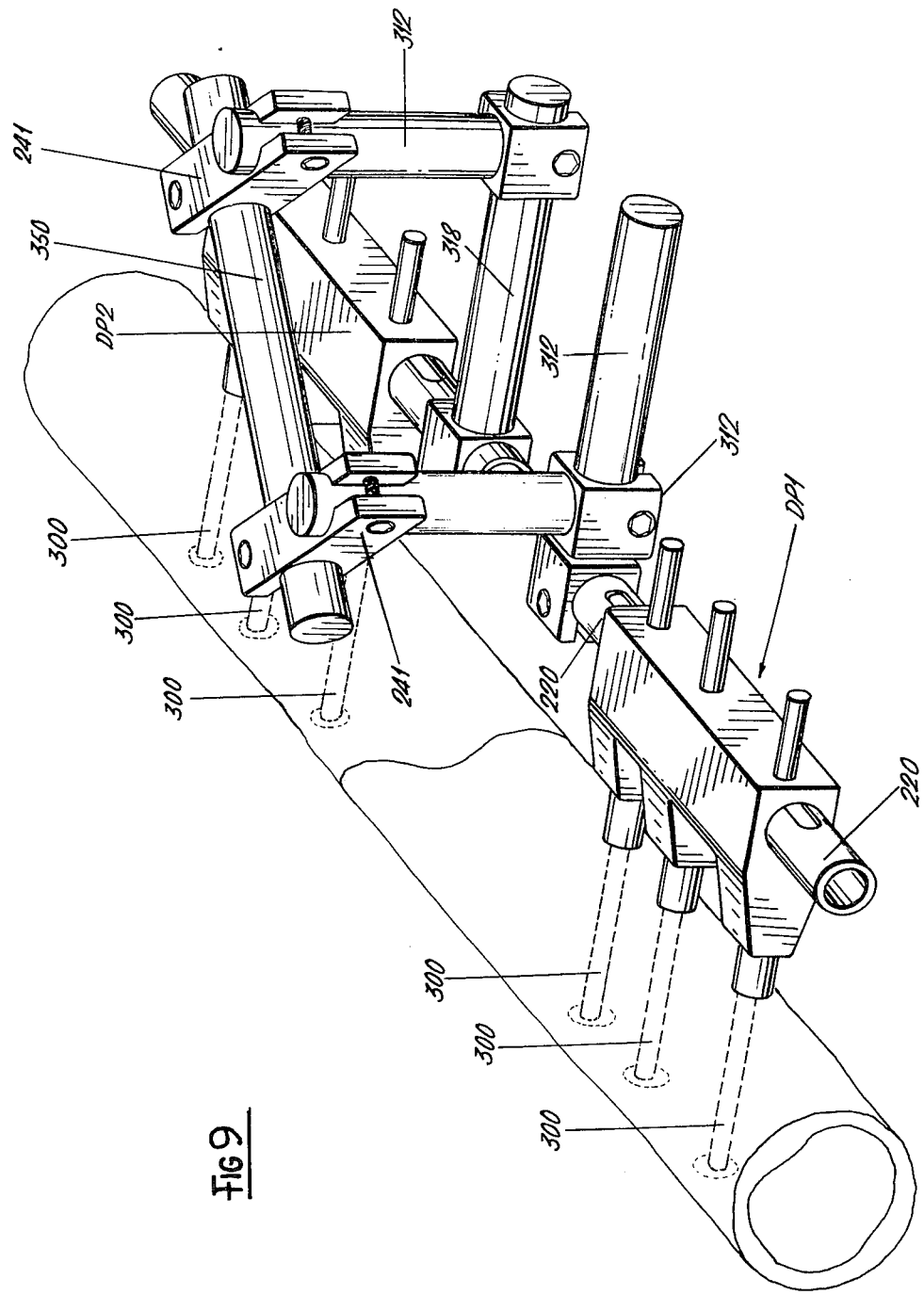
FIG. 9 is a similar view showing a second possible arrangement of some of the elements of the positioning system.

FIG. 9 shows a connecting system according to the invention, similar to the system shown in FIG. 2, wherein adjustable clamp members 211 are replaced by simple clamp members 312. Reviewing the unit, it can be seen that any rotating movement about the axes of holding device DP and of anyone of the illustrated clamps can be performed through suitable handles having a construction similar to the construction of clamp members 312. In order to obtain translatory movements along the axis of the clamp shanks, extractors can be used which are equal to the devices described in the prior application Ser. No. 801,305 wherein they are referred to as 110 to 114 as means for varying the position of the pins passing through the bone.

The arrangement of the connecting elements, as shown in FIG. 9, also represents one of the various possible arrangements allowing connecting bar 350 to be positioned in a direction perpendicular to the fracture surfaces. This is possible for any direction of these surfaces relative to the arrangement of the holding elements. Accordingly, it is readily evident that an interfragmentary pressure can be obtained by sliding clamps 241 along bar 350 and replacing this bar with an adjustable clamp member 211 of the type shown in FIG. 3. The object 3a stated at the beginning of this description can thus be reached.

From the above description and the drawings 1, 2, 8 and 9, it is evident that also object 3b can be reached. The joint unit can be positioned so that the axes of the movements allowed by the joints correspond to determined planes, selected as reference planes in order to determine, also and especially on two orthographic radiographic projections, the form of a fracture and the position of the relative bone fragments. With such an arrangement of the positioning system, an interfragmentary pressure on oblique (with respect to the reference planes) surfaces can be obtained as a resultant of two movements in two given directions.

It is also evident that with the arrangement according to the invention, while a separate movement in a given direction is performed, it is possible to keep the unit stationary in all other directions. This means that the mutual position of the bone fragments can be continuously controlled. Obviously, all the movements made possible are useful for obtaining the reduction of the fracture, applying and maintaining the interfragmentary pressure in the right direction and correcting possible displacements of the fragments caused by the application of the device.

Finally, it should also be noted that in operation, if the holding elements are applied on one side only of the bone, they are aligned as shown in FIG. 2 and a direct force is to be applied in directions laying on planes other than this plane, a rotating movement about the axis of device DP compensates for the inherent flexibility of these devices for exerting a holding action on the bone tissue.

Similarly, the pressure exerted along the axis of the bars of devices DP, aligned as shown in FIG. 2, can cause a deflection of the pins passing through the bone, thus determining an inclination of the fragments. This drawback should be eliminated either through an equal an opposed inclination about the axis of elements 211, or by urging the pins passing through the bone in the direction of their axis so that the fragment section adjacent to the fracture approaches the device and the fragment section remote from the fracture departs from the device.

From the above description it is evident that this system provides many possible arrangements which will be selected by those skilled in the art according to the biomechanical conditions of the specific case to be treated, yet keeping in mind the objects stated at the beginning of this description. It is also evident to those skilled in the art that in some cases all the movements made possible by this invention are not necessary. In all cases, however, the unit of the positioning joints described above can also be used only temporarily in order to position and stress holding devices DP with a force of optimal direction. This unit can easily and at any time replace or, vice-versa, be replaced by simplified connecting elements, such as ball joints, or by a part of the elements illustrated in this description and in patent application Ser. No. 801,305.

I claim:
1. A device for externally exerting a holding action on bone tissues comprising:
   (a) a plurality of means for engaging the bone and exerting a holding action thereon;
   (b) a plurality of at least three clamping means interconnecting said engaging and exerting means and for permitting rotational movement of said clamping means and said engaging and exerting means about a plurality of mutually perpendicular axes and axes inclined to the axis of the bone whereby said engaging and exerting means can engage the bone and exert a holding action at an inclined angle to the axis of the bone;
   (c) at least one of said clamping means including means for permitting said one clamping means to be translated along one of said axes whereby said one clamping means is movable in a translatable direction.
2. A device as defined in claim 1 including means for translating other of said clamping means along other of said axes.
3. A device as defined in claim 1 wherein at least one of said clamping means includes:
   (a) an elongated cylindrical shank thereon,
   (b) said shank having a threaded axial hole therein and a longitudinal groove on the external surface thereof,
   (c) said shank being slidably received within a hollow tubular body having a threaded end thereon,
   (d) a cap element being screwed on said threaded end,
   (e) said body having a substantially radial threaded hole therein,
   (f) a first screw inserted in said radial hole and received in said groove,
   (g) said shank having an axial opening therein,
   (h) a second screw having a head positioned between said cap and said body and extending into the axial opening of said shank.
4. A device as defined in claims 1, 2 or 3 including at least a pair of engaging and exerting means, said engaging and exerting means being connected together by a central substantially tubular body positioned with its axis perpendicular to the plane of the surface of the fracture.
5. A device as defined in claim 1 wherein one of said clamping means includes an elongated shank and means for adjusting the length of said shank.

* * * * *